(12) United States Patent
Blaga et al.

(10) Patent No.: US 7,651,599 B2
(45) Date of Patent: Jan. 26, 2010

(54) HIGH DENSITY FLUIDIC CHIP DESIGN AND METHOD OF SAMPLE INJECTION

(75) Inventors: Iuliu-Ioan Blaga, Fremont, CA (US); Jing Ni, Sunnyvale, CA (US); William D. Nielsen, San Jose, CA (US)

(73) Assignee: GE Healthcare (SV) Corp., Sunnyvale, CA (US)

( * ) Notice: Subject to any disclaimer, the term of this patent is extended or adjusted under 35 U.S.C. 154(b) by 1035 days.

(21) Appl. No.: 10/528,864

(22) PCT Filed: Sep. 25, 2003

(86) PCT No.: PCT/US03/30362

§ 371 (c)(1),
(2), (4) Date: Mar. 23, 2005

(87) PCT Pub. No.: WO2004/029580

PCT Pub. Date: Apr. 8, 2004

(65) Prior Publication Data

US 2008/0169193 A1      Jul. 17, 2008

Related U.S. Application Data

(60) Provisional application No. 60/413,523, filed on Sep. 25, 2002.

(51) Int. Cl.
*G01N 27/26* (2006.01)

(52) U.S. Cl. .................. 204/453; 204/451; 204/601; 204/604

(58) Field of Classification Search .......... 204/451, 204/453, 604, 601
See application file for complete search history.

(56) References Cited

U.S. PATENT DOCUMENTS

| | | | |
|---|---|---|---|
| 5,104,512 A | 4/1992 | Gombocz et al. | |
| 6,086,740 A * | 7/2000 | Kennedy | ............ 204/601 |
| 6,103,199 A | 8/2000 | Bjornson et al. | |
| 6,143,152 A | 11/2000 | Simpson et al. | |
| 6,375,817 B1 | 4/2002 | Taylor et al. | |
| 6,485,625 B1 | 11/2002 | Simpson et al. | |
| 6,488,895 B1 | 12/2002 | Kennedy | |
| 6,533,914 B1 | 3/2003 | Liu | |
| 6,623,613 B1 | 9/2003 | Mathies et al. | |

FOREIGN PATENT DOCUMENTS

WO       WO98/55852       12/1998

* cited by examiner

*Primary Examiner*—Nam X Nguyen
*Assistant Examiner*—J. Christopher Ball
(74) *Attorney, Agent, or Firm*—Yonggang Ji

(57) ABSTRACT

The present invention discloses a high-density parallel channel design for a microfabricated capillary array electrophoresis chip, with vertical T or double T design for sample injection. An alternative embodiment of the invention includes a closed buffer reservoirs with integrated electrodes and buffer feeding ports. Also disclosed are novel sample loading and injection methods, including the use of using either a capillary array connected to an electrode, or an array of metal pens as the loader/electrode.

13 Claims, 8 Drawing Sheets

HIGH DENSITY FLUIDIC CHIP DESIGN AND METHOD OF SAMPLE INJECTION

CROSS REFERENCE TO RELATED APPLICATIONS

This application is a filing under 35 U.S.C. § 371 and claims priority to international patent application number PCT/US2003/030362 filed Sep. 25, 2003, published on Apr. 8, 2004 as WO 2004/029580 and also claims priority to U.S. provisional application No. 60/413,523, filed Sep. 25, 2002; the disclosures of which are incorporated herein by reference in their entireties.

FIELD OF THE INVENTION

The present invention relates generally to the field of microfluidic chips. More particularly, the present invention relates to a microfluidic chip having a vertical T design. The invention also relates to novel sample injections methods.

BACKGROUND OF THE INVENTION

Increasingly, biological fragment separations demand cost-effective high-throughput, high-performance technologies. Sample fragment separations using slab gel technology has been supplanted by capillary array electrophoresis (CAE). The throughput of a CAE system is directly proportional to the number of separation capillaries in the instrument. However, as the number of capillaries increases, it becomes more challenging to control sample injection and to detect signals from all of the capillaries.

Another technology for high-throughput DNA analysis is capillary array electrophoresis on microchips. Microchips are planar members typically formed from a glass, silica, or even polymeric material. Photolithographic techniques are typically used to microfabricate CAE channels on substrates. The microchip substrate defines at least one elongate capillary channel which extends between opposed cathode and anode ports. Sample and waste ports are located adjacent the cathode port and channel segments extend therefrom to the elongate micro-channel. D. Harrison et al., Anal. Chem. 64, 1926-1932; Z. Fan et al., Anal. Chem. 66, 177-184; and S. Jocobson et al., Anal. Chem. 66, 1107-1113. When a biological, fluid sample is deposited in the sample port, electrical potential may be applied to the four ports so as to direct a portion of the fluid sample first into the elongate micro-channel and then towards the opposed anode port. These design is often called 'T' or "twin T" injection scheme. The fluid sample, which separates into different-length segments, is analyzed as it passes a point in the channel at which is read by an interrogation device. Microchips have been used in separation of not only biological samples, but also chemicals as well. For example, microchips have been used to separate fluorescent dyes, fluorescently-labeled amino acids, DNA restriction fragments, PCR products, short oligonucleotides, short tandem repeats, and DNA sequencing fragments.

In order to increase throughput, multiple CAE channels have been microfabricated on microchips and used for DNA fragment size analysis. Channels on many substrate designs include right angle turns that work well for fragment sizing but which degrade performance in sequencing separations. Alternate designs, using a round substrate, include radially-extending channels terminating at a common, centrally-located anode. For example, Shi et al. in Anal. Chem. 1999, 71, 5354-5361, disclose a 96 channel radial CAE microchip design for use with a rotary confocal fluorescence detection system. The 96 channels are formed on a 10 centimeter diameter Borofloat substrate so as to extend from a common, centrally-located anode. Such a design makes effective use of the chip space in providing uniform-length channels while still allowing a detector to scan perpendicularly across all of the channels. One drawback to this design, however, is that the effective channel lengths are limited to less than one-half of the chip diameter, or here to 3.3 centimeters for a 10 centimeter diameter chip. The effective channel length refers to the distance a fluid would travel through a channel before reaching the point where it is interrogated by an analytical device. While channels of this length work well for separations of certain restriction fragments and genotyping samples, it is very challenging to achieve sequencing separations using such short channels. In order to increase the length of the channels, larger-diameter chips may obviously be used, however the fabrication costs of suitable larger chips can be cost-prohibitive.

One of the limitations of the current micro-channel plate (MCP) design for chemical/biological sample separation lies in the maximum density of channels on a plate. The area of the interface holes limits the channel density on the actual chips, therefore the throughput of separation and the detection. Such a limitation is intrinsic to the horizontal "T" or "double T" injection design.

In the case of short channels on chips, the injected sample plug properties are essential for a good separation. It has to be short enough to produce a good resolution and concentrated enough for a processable signal.

The use of the conventional pipette or syringe based fluid transfer method for sample loading to the MCP channel is another area needs improvement. The matrix in the sample well has to be removed before sample loading. Fluid control equipment is required to clean the tip of the pipette. In practice, this system proves to be complex, as well as costly.

There is therefore a need in the art for a cost-effective high-throughput, high-performance electrophoresis microchip which maximizes formation of uniform-length, elongate electrophoresis separation microchannels thereon. There is also a need in the art for an electrophoresis microchip which provides a compact array of microchannels so as to increase throughput. There is still another need of improved sample injections methods.

SUMMARY OF THE INVENTION

It is the aim of this invention to: (1) develop an alternative system to the traditional double T injection design that offers higher channel density; (2) develop novel sample loading and injection methods that offers unique advantage to the conventional method; and (3) provide a combined system for a high density microchannel separation system.

One embodiment of the present invention is a high density capillary array electrophoresis plate, comprising: (1) an array of parallel microfabricated separation channels formed on a surface of a first microfabricated substrate and a corresponding surface of a second substrate bonded to the surface of said first substrate, each of said channels having a first end and a second end; (2) an array of sample ports on a first surface of said capillary array electrophoresis plate; and (3) an array of sample passageways connecting said array of sample ports and said array of separation channels, wherein each of said array of sample passageways is perpendicular to said first surface of said capillary array electrophoresis plate; wherein each separation channel of the plurality of separation channels is in fluid communication with at least one dedicated sample port through one of said array of sample passageways.

In addition, the high density capillary array electrophoresis plate may further include: (1) an array of waste ports on a second surface of said capillary array electrophoresis plate; (2) an array of waste passageways connecting said array of waste ports and said array of separation channels, wherein each of said array of waste passageways is perpendicular to said second surface of said capillary array electrophoresis plate; (3) a waste reservoir mount mounted on said second surface of said capillary array electrophoresis plate; and (4) at least one electrode coupleable to said waste reservoir mount; wherein each separation is channel of the plurality of separation channels is in fluid communication with said waste reservoir through one of said array of waste ports.

In one aspect, each of the array of sample passageways and each of said array of waste passageways forms a single passageway, connecting to one of said array of microfabricated separation channels.

In another aspect, the array of sample ports are regularly spaced on the plate and adapted to engage a parallel loading device. The parallel loading device comprises an array of capillaries, or an array of metal pens.

Additionally, the present capillary array electrophoresis plate further comprises an array of cathode ports on the first surface of said capillary array electrophoresis plate, each connected to said first end of each of the separation channels; and an array of anode ports on the first surface of said capillary array electrophoresis plate, each connected to said second end of each of the separation channels. In addition, electrode arrays are coupled to each of said cathode and anode ports.

Alternatively, the present capillary array electrophoresis plate further comprises a common cathode reservoir connected to said first end of each of the separation channels; a common anode reservoir connected to said second end of each of the separation channels; an electrode for said common cathode reservoir; and an electrode for said common anode reservoir. The common anode and cathode reservoirs could be enclosed and each has a buffer loading port on the first surface of said capillary array electrophoresis plate.

Another embodiment of the present invention is a high density capillary array electrophoresis plate system, comprising: (1) a capillary array electrophoresis plate including: an array of parallel microfabricated separation channels formed on a surface of a first microfabricated substrate and a corresponding surface of a second substrate bonded to the surface of said first substrate, each of said channels spans the full length of the plate and has a first end and a second end; (2) an array of sample ports on a first surface of said capillary array electrophoresis plate; (3) an array of sample passageways connecting said array of sample ports and said array of separation channels, wherein each of said array of sample passageways is perpendicular to said first surface of said capillary array electrophoresis plate; (4) a cathode mount attached to the first end of said capillary array electrophoresis plate; (5) an anode mount attached to the second end of said capillary array electrophoresis plate; (6) an electrode in said cathode mount; and (7) an electrode in said anode mount; wherein each separation channel of the plurality of separation channels is in fluid communication with at least one dedicated sample port through one of said array of sample passageways.

Another embodiment of the present invention relates to a method of forming a capillary array electrophoresis plate, comprising: (1) forming an array of microfabricated separation channels having a first end and a second end; (2) forming an array of sample ports on a first surface of said capillary array electrophoresis plate; (3) connecting the array of sample ports to the array of microfabricated separation channels through an array of sample passageways; (4) forming an array of cathode ports on the first surface of said capillary array electrophoresis plate, each connected to said first end of each of the separation channels; (5) forming an array of anode ports on the first surface of said capillary array electrophoresis plate, each connected to said second end of each of the separation channels; (6) connecting an electrode array to each of said array of cathode ports; and (7) connecting an electrode array to each of said array of anode ports.

An alternative method of forming a capillary array electrophoresis plate comprises: (1) forming an array of microfabricated separation channels having a first end and a second end; (2) forming an array of sample ports on a first surface of said capillary array electrophoresis plate; (3) connecting the array of sample ports to the array of microfabricated separation channels through an array of sample passageways; (4) connecting a common cathode reservoir to said first end of each to of said array of separation channels; (5) connecting a common anode reservoir to said second end of each of said array of separation channels; (6) connecting an electrode to said cathode reservoir; and (7) connecting an electrode to said anode reservoir.

Yet another alternative method of forming a capillary array electrophoresis plate comprises: (1) forming a capillary array electrophoresis plate including: an array of parallel microfabricated separation channels formed on a surface of a first microfabricated substrate and a corresponding surface of a second substrate bonded to the surface of said first substrate, each of said channels spans the full length of the plate and has a first end and a second end; (2) forming an array of sample ports on a first surface of said capillary array electrophoresis plate; (3) connecting said array of sample ports and said array of separation channels through an array of sample passageways, wherein each of said array of sample passageways is perpendicular to said first surface of said capillary array electrophoresis plate; (4) attaching a cathode mount to the first end of said channels; (5) attaching an anode mount to the second end of said channels; (6) coupling an electrode in said cathode mount; and (7) coupling an electrode in said anode mount; wherein each separation channel of the plurality of separation channels is in fluid communication with at least one dedicated sample port through one of said array of sample passageways.

In addition, the method of forming a capillary array electrophoresis plate of the present invention may include: (1) forming an array of waste ports on a second surface of said capillary array electrophoresis plate; (2) connecting the array of waste ports and the array of separation channels through an array of waste passageways, wherein each of said array of waste passageways is perpendicular to said second surface of said capillary array electrophoresis plate; (3) forming a waste reservoir mount; (4) mounting said waste reservoir mount on said second surface of said capillary array electrophoresis plate; and coupling at least one electrode to said waste reservoir mount; wherein each separation channel of the plurality of separation channels is in fluid communication with said waste reservoir through one of said array of waste ports.

Yet another embodiment of the present invention relates to a method for injecting multiple samples into separation channels on a capillary array electrophoresis plate, comprising: (1) forming an array of microfabricated separation channels having a first end and a second end; (2) forming an array of sample ports on a first surface of said capillary array electrophoresis plate; (3) connecting the array of sample port to the array of microfabricated separation channels through an array of sample passageways; (4) connecting a common cathode reservoir to said first end of each of said array of separation channels; (5) connecting a common anode reservoir to said second end of each of said array of separation channels; (6) connecting an electrode to said cathode reservoir; (7) connecting an electrode to said anode reservoir; (8) loading an array of capillaries with sample solutions; (9) contacting each of said array of capillaries with a sample port of said array of sample ports; and (10) applying an injection voltage between the sample capillary and the anode reservoir to draw the sample into the separation channels.

Still another embodiment of the present invention relates to a method for injecting multiple samples into separation channels on a capillary array electrophoresis plate, comprising: (1) forming an array of microfabricated separation channels having a first end and a second end; (2) forming an array of sample ports on a first surface of said capillary array electrophoresis plate; (3) connecting the array of sample port to the array of microfabricated separation channels through an array of sample passageways; (4) attaching a cathode mount to the first end of said channels; (5) attaching an anode mount to the second end of said channels; (6) coupling an electrode in said cathode mount; (7) coupling an electrode in said anode mount; (8) loading an array of capillaries with sample solutions; (9) contacting each of said array of capillaries with a sample port of said array of sample ports; and (10) applying an injection voltage between the sample capillary and the anode reservoir to draw the sample into the separation channels.

Another embodiment of the present invention relates to a method for injecting multiple samples into separation channels on a capillary array electrophoresis plate, comprising: (1) forming an array of microfabricated separation channels having a first end and a second end; (2) forming an array of sample ports on a first surface of said capillary array electrophoresis plate; (3) connecting the array of sample port to the array of microfabricated separation channels through an array of sample passageways; (4) connecting a common cathode reservoir to said first end of each of said array of separation channels; (5) connecting a common anode reservoir to said second end of each of said array of separation channels; (6) connecting an electrode to said cathode reservoir; (7) connecting an electrode to said anode reservoir; (8) loading an array of metal pens with sample solutions; (9) contacting each of said array of pens with a sample port of said array of sample ports; (10) applying an injection voltage between the pens and the anode reservoir to draw the sample into the separation channels.

Another embodiment of the present invention relates to a method for injecting multiple samples into separation channels on a capillary array electrophoresis plate, comprising: (1) forming an array of microfabricated separation channels having a first end and a second end; (2) forming an array of sample ports on a first surface of said capillary array electrophoresis plate; (3) connecting the array of sample port to the array of microfabricated separation channels through an array of sample passageways; (4) attaching a cathode mount to the first end of said channels; (5) attaching an anode mount to the second end of said channels; (6) coupling an electrode in said cathode mount; (7) coupling an electrode in said anode mount; (8) loading an array of metal pens with sample solutions; (9) contacting each of said array of pens with a sample port of said array of sample ports; (10) applying an injection voltage between the sample pen and the anode reservoir to draw the sample into the separation channels.

DETAILED DESCRIPTION OF THE PREFERRED EMBODIMENT

Figure 1A:
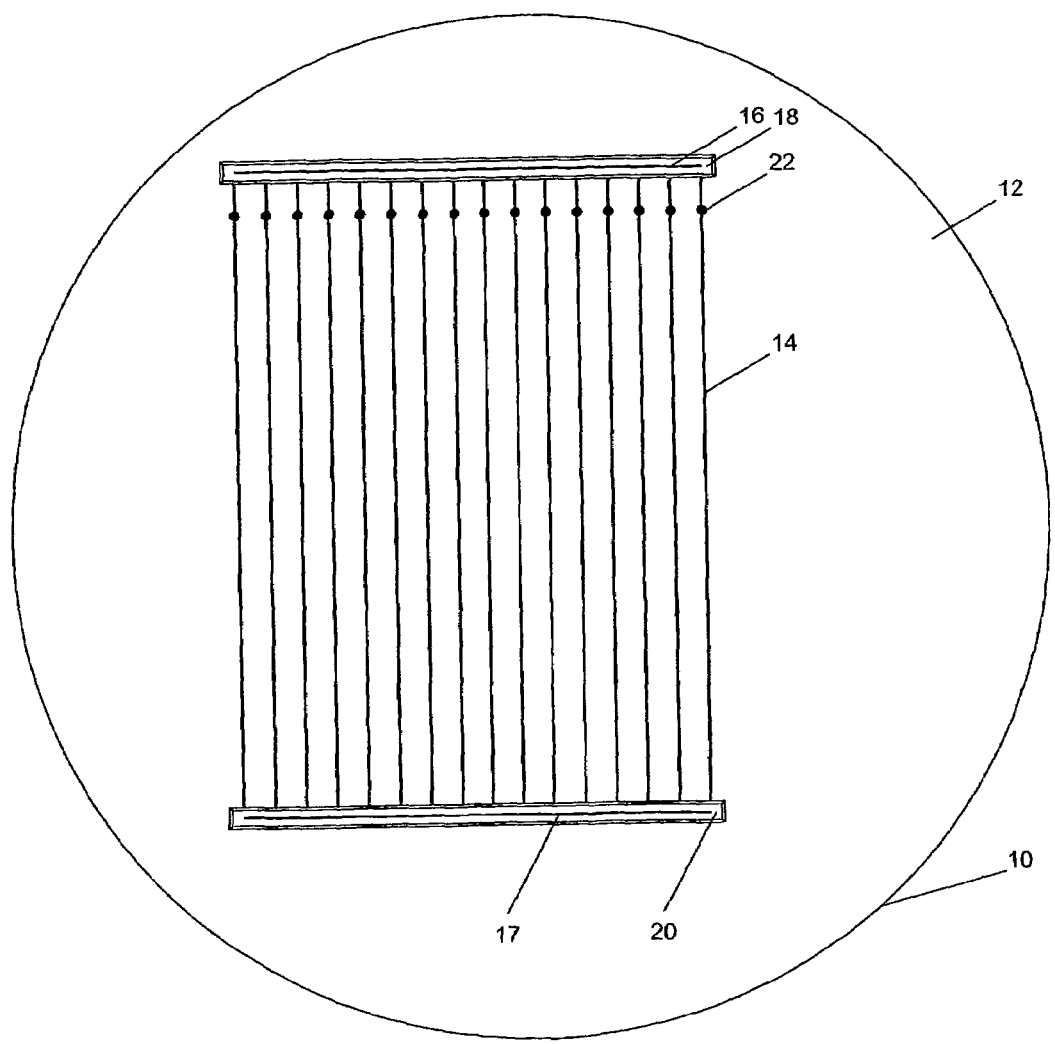
FIG. 1A depicts the arrangement of microchannels on a first substrate in accordance with one embodiment of the present invention.

FIG. 1 depicts a round substrate 10 on which an array of parallel micro separation channels 14 of the present invention is formed. Substrate 10 is desirably formed of a material suitable for electrophoresis separation including, by way of illustration and not of limitation, glass, silica, or a polymeric material. Substrate 10 may be formed using photolithographic techniques as is known in the art. While shown to be circular in shape, the present invention further contemplates that substrate 10 may be formed in any shape suitable for an electrophoresis separation device.

The present invention contemplates forming substrate 10 having a planar first major surface 12 which defines elongate separation channels 14. Each separation channel 14 is also in fluidic communication with an analyte loading port 22 that extends to the upper surface of substrate 10. Each of the separation channels 14 extends in fluid communication from a cathode port and extends in fluid communication from an anode port. Each of cathode and anode ports contains an electrode to provide positive or negative voltage. In a preferred embodiment as in FIG. 1A, the parallel separation channels of a substrate share a common cathode port 18 and a common anode port 20, with an electrode 16, 17 in each port.

Figure 1B:
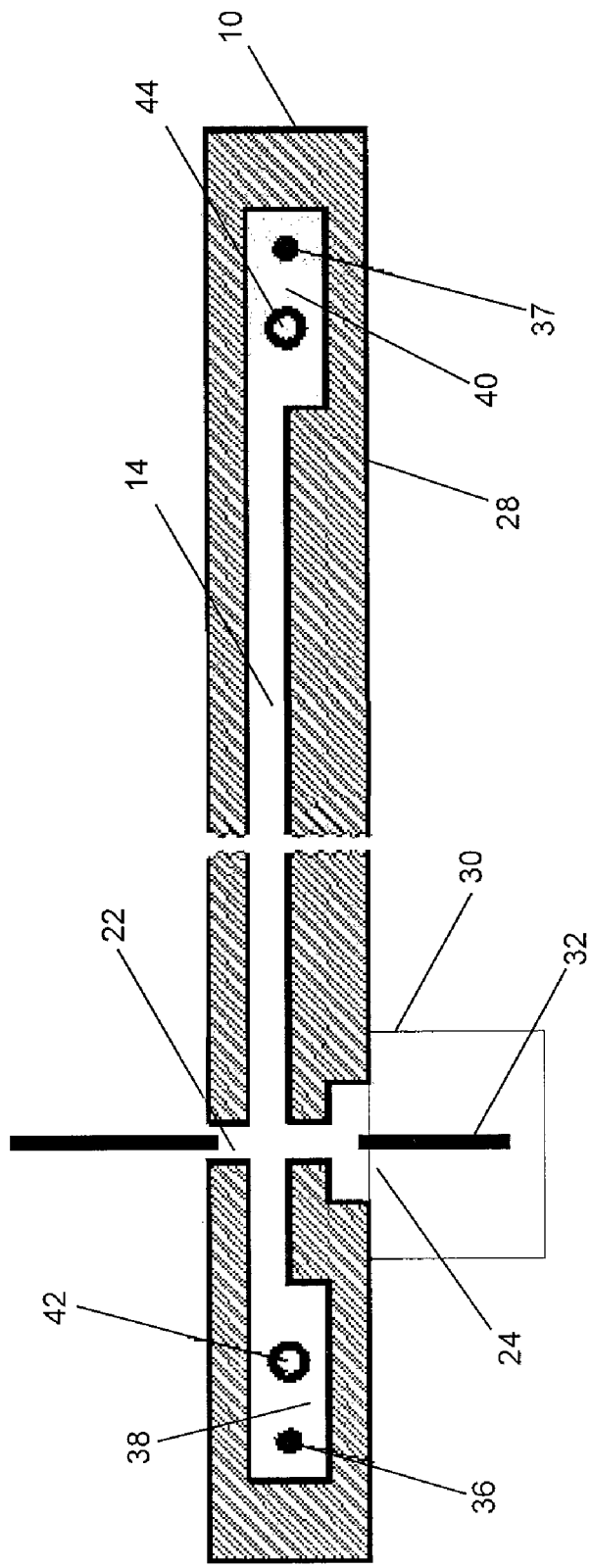
FIG. 1B shows a cross-section view of another embodiment of the current invention.

An alternative to the common cathode and anode port scheme of FIG. 1A is shown in FIG. 1B, in a cross section view. Here, closed reservoirs 38, 40 are designed for holding buffer at both cathode and anode end, with one or more buffer loading port 42, 44 at each end. This allows a continuous feed of buffer. In this way the buffer capacity and the current will be constant, providing uniform separation conditions over the run time. The closed reservoirs also eliminate evaporation issues so that high temperature separations are possible. The integrated electrodes 36, 37 will facilitate the handling and mounting of the chip into the analytical instrument.

The present invention further contemplate a variation of the scheme of FIG. 1A and FIG. 1B. The common cathode and anode reservoirs and the associated electrodes can be separated from the parallel separation channels 14 of substrate 10, as fluidic/voltage adapters. The adapters, when connected to substrate 10, connect the separation channels with the anode and cathode buffers.

Furthermore, a waste port 24 may be introduced from the bottom surface 28 of substrate 10 to connect with the analyte loading port 22. Waste port 24 may reside directly under the loading port 22 so that they form a continuous vertical channel through substrate 10. More preferably, waste port 24 is formed slightly upstream or down stream of the loading port, to form a vertical double T structure. In either case, both the loading port and the waste port extend into the separation channel at a right angle. In the case where a waste port 24 is incorporated in the design (FIG. 1B), a slot 30, which serves as a common waste reservoir, can be milled on the surface of the bottom plate 28, to connect all the bottom holes. A common waste electrode 32 can be placed in the slot to control the voltage in the waste ports.

The spacing between channels is defined by the injection well diameter. The channels are symmetrical and parallel, fact that should provide identical separation conditions. The symmetry was extended to the cathode and the anode areas also.

Individual cathode ports and waste ports are desirably formed having a diameter in the range of about 500 microns to about 1.2 millimeters. Individual anode ports are desirably formed having a diameter of about 1 to about 2 millimeters. Each separation channel is desirably formed having a width of about 10 microns to about 500 microns, preferably about 110 microns.

In search of a simpler and cheaper sample-loading device, a couple of devices are identified as capable of replacing the conventional fluid transfer methodology. One is a capillary array, and the other is a pen type device. Both offer unique advantages over the conventional methods such as by pipetting.

U.S. Pat. No. 6,423,536 discloses an automated capillary array system for preparing nanoscale reactions and transferring such, the disclosure of which is incorporated herein by reference of its entirety. The present invention contemplates the use of such a system as part of a sample loading system for the separation chip.

The system uses a capillary cassette comprised of a number of capillary tube segments arranged in parallel alignment. The tube segments extend through a substrate and are generally positioned with uniform spacing. The capillaries are most commonly spaced such that there is a one to one relationship between a capillary and a sample loading port of the microfluidic chip. One end of the capillary tube is connected to a buffer reservoir where an injection electrode is placed for electrokinetical injection of the analyte. Following each use, the capillary cassette may be placed into a capillary cassette washer and washed. Following washing, the capillary cassette may be reused.

An alternative to the capillary array sample loaders is the use of a metal microarray spotter pen (or pin) type device. The pen loading method offers several advantages over the conventional method. The size of the sample well is greatly reduced, so the channel density of a given plate is further increased. The pen device is used as a sample injection electrode, in addition to a loading tip, therefore eliminates one operating step. The amount of sample transferred is also greatly reduces, making the device particularly useful in dealing with small amount, non-reproducible samples. One kind of pens suitable is described in U.S. Pat. No. 5,770,151, the disclosures of which are hereby incorporated by reference in its entirety.

Similar results can be achieved by using different pen designs. A preferred pen design is described in a co-pending U.S. patent application Ser. No. 10/029,737, the disclosures of which are hereby incorporated by reference in its entirety.

Figure 2:
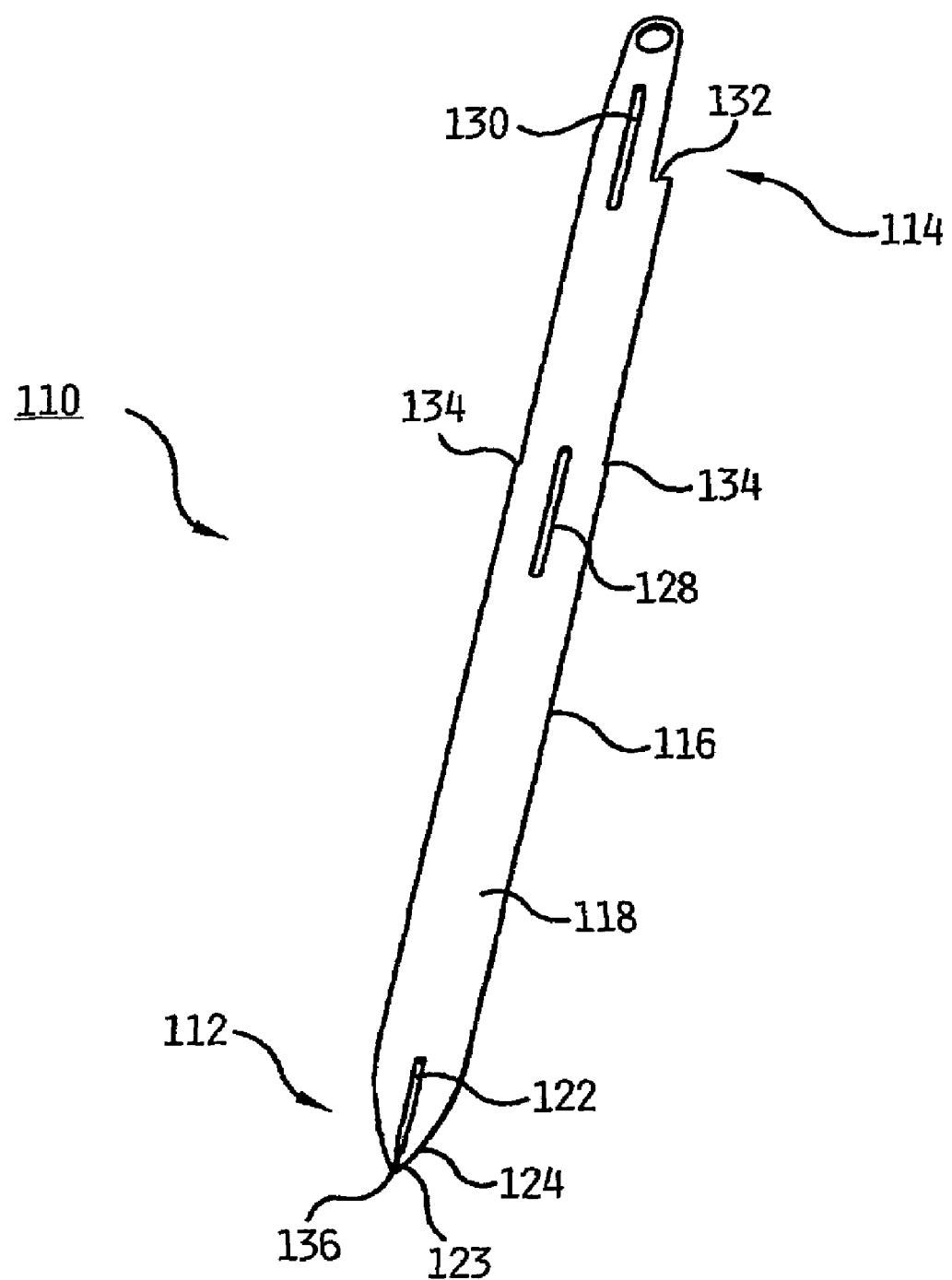
FIG. 2 is a perspective view of a sample loading pen of the present invention.
Figure 3:
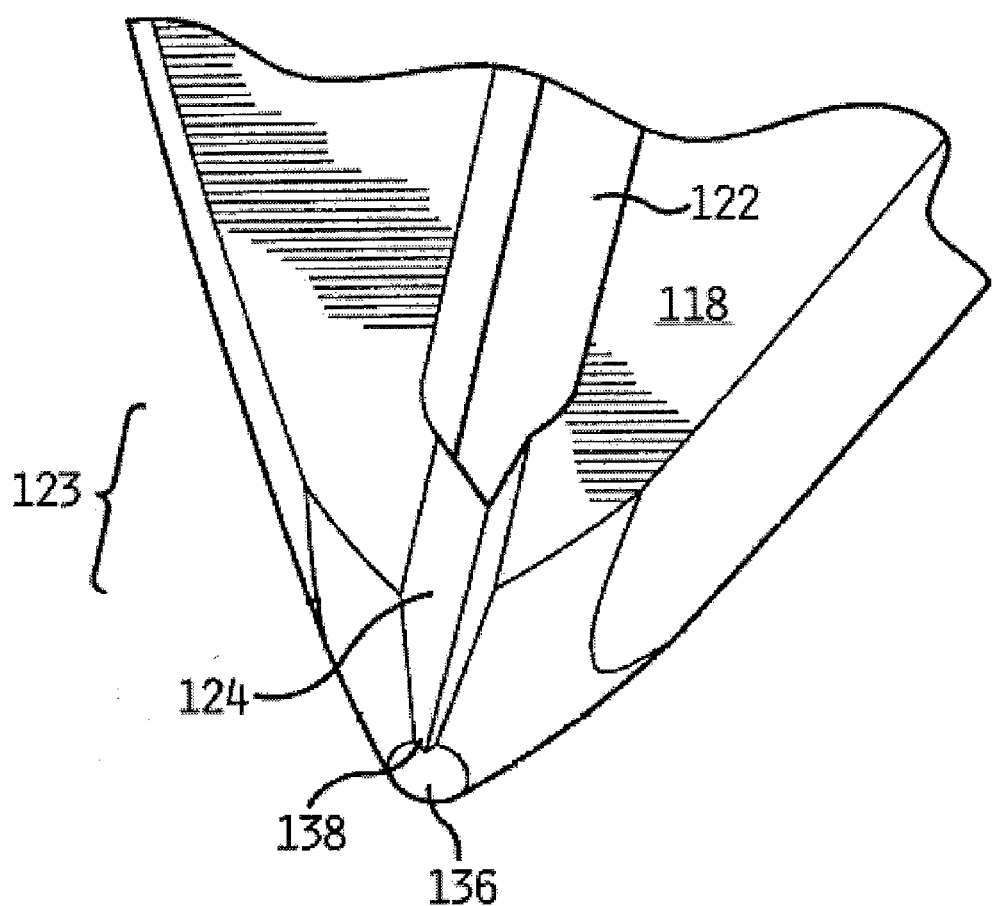
FIG. 3 is a perspective view of the tip of the sample loading pen of FIG. 2.

FIG. 2 depicts a dispensing pen 110 of the present invention, according to U.S. patent application Ser. No. 10/029, 737. Pen 110 includes a dispensing end 112, an opposed adaptor end 114, and an elongate pen body 116 extending therebetween. Pen body 116 is desirably fabricated by a photochemical machining process commonly used in the printed circuit board industry for high volume fabrication of flat, highly intricate metal parts. Pen 110 is desirably formed from type 304 stainless steel, full hard, although most other 300 series stainless steels are contemplated as being suitable.

Pen 110 is a substantially planar member having opposed first major surface 118 and second major surface 120. Pen body 116 defines a fluid reservoir 122, a dispensing tip 123, and an elongate fluid channel 124 extending therebetween. Fluid reservoir 122 and fluid channel 124 open toward first major surface 118. A fluid to be dispensed is drawn through channel tip 123 into channel 124 and reservoir 122 when loading pen 110. Pen body 116 includes the means for cooperating with a pen holding device for retaining pen 110 throughout dispensing operations. Adaptor end 114 of pen body 116 defines mounting apertures 128 and 130 and abutment shoulders 132 and 134 for cooperatively engaging a pen holding device.

Fluid channel 124 may be mechanically fabricated by cutting a groove down from reservoir 122 to strike surface 136 using a carbide cutting tool. The groove ranges from 0.001" to 0.002" deep, and has a 60 degree included angle. The groove may also be machined in by using a grinding wheel, slitting saw, coined in place with a stamping operation, or by any other method known to those skilled in the fabrication arts. Alternatively, fluid channel 124 may be etched in during the initial etching step for pen body 116. Fluid channel 124 through major surface 118, resulting in an open groove half way through the body. Pens of the present invention that have been fabricated by half etching have shown good potential for an extremely low cost, medium density pen.

The material used to form a pen body of the present invention desirably exhibits good mechanical strength and corrosion resistance. The material should also etch easily so as to allow formation of the fluid conducting components of the pen as well as the mechanical retention means of adaptor end 114. The pens are desirably manufactured from type 304 stainless steel, full hard, although most other 300 series stainless steels are contemplated as being acceptable. Heat treatable stainless steels may be employed although corrosion may need to be controlled. Beryllium copper offers excellent mechanical properties for a pen of the present invention. Plating would be required for corrosion control.

Pen body 110 is desirably formed to be about 0.005 inches thick, i.e. between major surfaces 118 and 120. Fluid channel 124 is desirably formed to be about 0.0015 inches across at major surface 118 and in range of about 0.001 inches to 0.003 inches deep from major surface 118. Fluid channel 124 is shown to have a V-shape although other channel shapes are contemplated by the present invention. Fluid channel 124 and fluid reservoir 122 desirably hold in the range of about 5 to about 100 nanoliters and may be formed to hold about 60 nanoliters of fluid sample.

A fluid to be dispensed by pen 110 is drawn and dispensed through dispense aperture 138 and into fluid channel 124 by capillary action. Fluid drawn into fluid reservoir 122 is retained there by surface tension forces. During dispensing operations, as pen 110 is brought into contact with buffer in a loading port, electric potential between the pen and the anode electrode cause charged analytes to be transferred into the separation channel.

The pen bodies should be cleaned before each use to remove any residual contaminants from the fabrication processes or the previous use. This is accomplished by in an ultrasonic cleaner using 95% ethanol. It is followed by a deionized water rinse. The surface of the stainless steel should be passivated to remove imbedded surface contaminants from the fabrication process as well as to improve corrosion properties. Passivation can be accomplished by immersing the pen in a 2M solution of Potassium Hydroxide, followed by immersing in concentrated Nitric Acid. Treatment can also be accomplished with a two part solution of 2M Potassium Iodide and 20% Hydrogen Peroxide. Electropolishing using a solution of Phosphoric Acid and Sulfuric Acid and inducing an electric potential also gives excellent passivation results.

Figure 4:
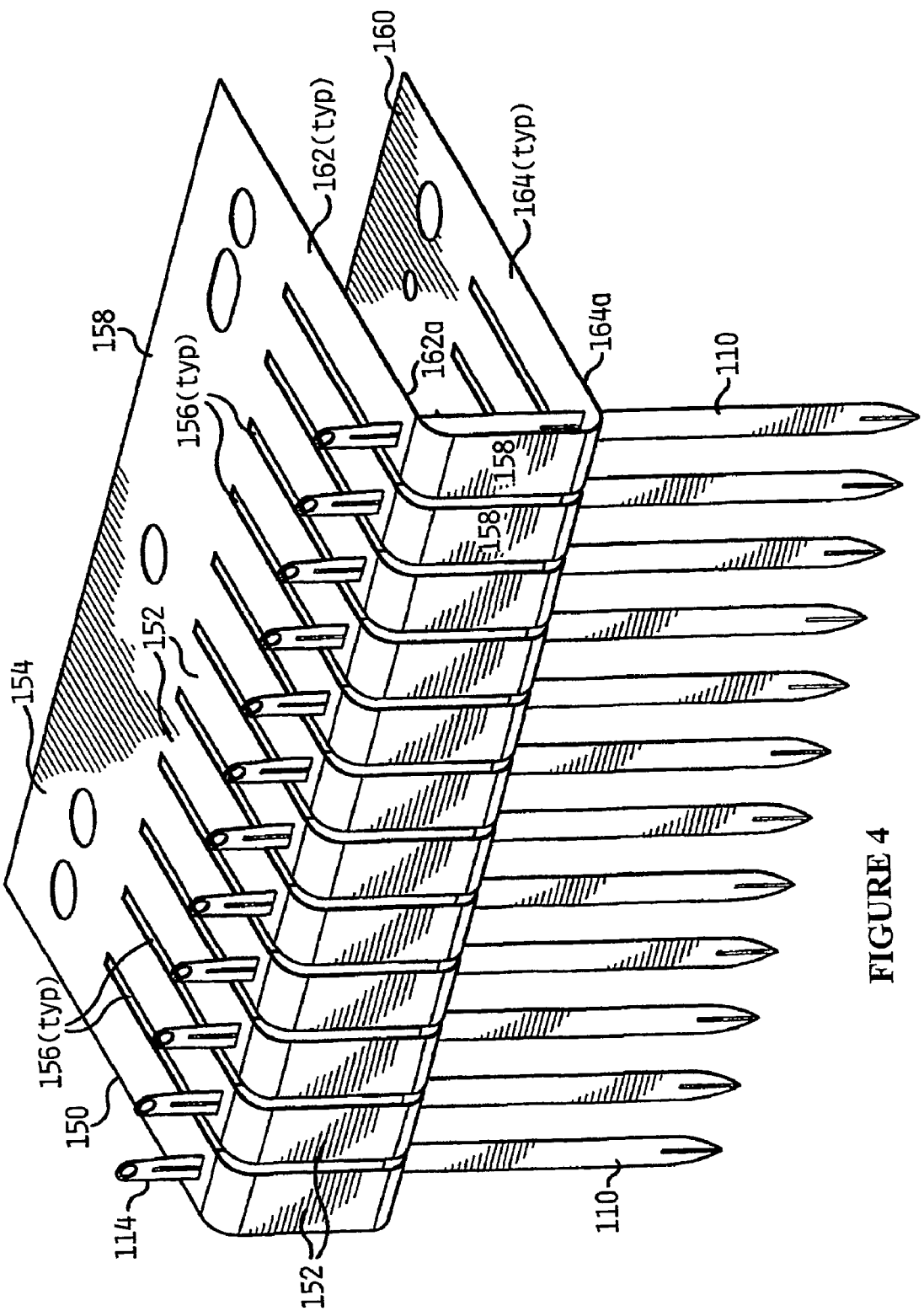
FIG. 4 is a perspective view of a pen-holder assembly of the present invention containing twelve pens.

FIG. 4 depicts a cantilever twin beam flexure pen holder assembly 150 for accommodating a number of pens of dispensing pens. While FIG. 4 shows pen holder assembly 150 supporting twelve disensing pens 110 of the present invention, it is contemplated that pen holder assembly may accommodate other pen designs as well. Manifold pen holder assembly includes a number of cantilever holding arms 152, each for independently retentively supporting a dispensing pen 110.

Pen holder assembly 150 is desirably formed from a sheet metal body 154 which is cut and bent to provide an elongate slot 156 between adjacent holding arms 152. Each holding arm 152 extends between opposed first and second transversely-extending bases 158 and 160. Body 154 is bent to form, in each cantilever holding arm 152, a face 155 supporting a pair of transversely-spaced elongate beams 162 and 164 extending from face 155 to bases 158 and 160, respectively.

Each pair of beams 162 and 164 include a distal end 162a and 164a, respectively, adjacent a face 155. Each distal end 162a and 164a of each beam 162 and 164 defines a pen accommodating aperture in spaced overlying registry for receiving and retaining the adaptor end 114 of a dispense pen 110 therethrough.

Pen holder assembly 150 is retained by an applicating machine, not shown, used to dispense a sample fluid from each of the pens into an array of loading ports. The applicating machine may also control the loading of a fluid into the pens as well as the cleaning of the pens between sample loads.

An array of pens in a pen holder assembly is dipped in a sample solution in the wells of standard 96 or 384 well plates, and moved to the top of the micro-channel plate. The pens are pre-aligned with the sample loading ports (wells) of the micro-channel plate, so that when they are lowered, they are inserted into each port. In the single T injection scheme (where no waste port is present), injection voltages are applied to the sample loading pen and the anode. In the double T injection scheme (where waste port is present), injection voltages are applied to the sample loading pen and the electrode in the waste reservoir. Bias voltages can be applied to the cathode and anode to prevent sample leaking. During the injection process, samples are electropheretically transferred from the pens into the fluidic channels.

Single injection approach: When the sample loading is complete, voltages on the pens and other electrodes can be switched for separation. In this process, the injected samples move toward the anode and are being separated in the main parallel channels. The pens and/or electrode in the waste reservoir are provided with voltages to prevent sample leaking.

Multiple injection approach: Alternatively, after sample loading is complete, pens can be moved away from the sample wells. If necessary, the sample wells can be cleaned and filled with fresh buffer. Separation voltages are applied to the common electrodes. As the first group of samples is being separated in the channels, the pens can be cleaned and dipped in the second group of samples. The separation can be temporarily stopped, when the loaded pens come back to the plate to perform another injection, then resume again. The two groups of samples are now being separated simultaneously, but are spatially separated by a distance in the channel. Multiple injections can be performed sequentially until the end of the matrix lifetime.

EXAMPLES

The following examples illustrate certain preferred embodiments of the illustration that are not intended to be illustrative of all embodiments.

Example 1

Sample Separation Using the Vertical T Design

A glass wafer was micro-fabricated using the standard photolithographic and etching procedure. Effenhauser et al. *Anal. Chem.* 65:2637-2642 (1993). Two millimeter cathode and anode holes were drilled at each end of a channel. Point seven-five millimeter sample loading holes were drilled at 5 mm down-stream to the cathode port. The channels were derivatized and loaded with LPA matrix by using a high pressure clamping/loading system. The sample loading hole was flushed with water.

The plate is then placed in a fluidic/voltage adapter to connect with anode and cathode buffers at each end of the plate.

A 5 cm capillary was loaded with single color M13 standard. It was connected to a buffer reservoir at one end, and the other end of the capillary was placed into the injection hole (sample loading hole). An injection voltage was applied between the buffer reservoir and the anode. After sample injection, the injection hole was cleaned and buffer was added. A run voltage was then applied to the cathode hole.

Figure 5:
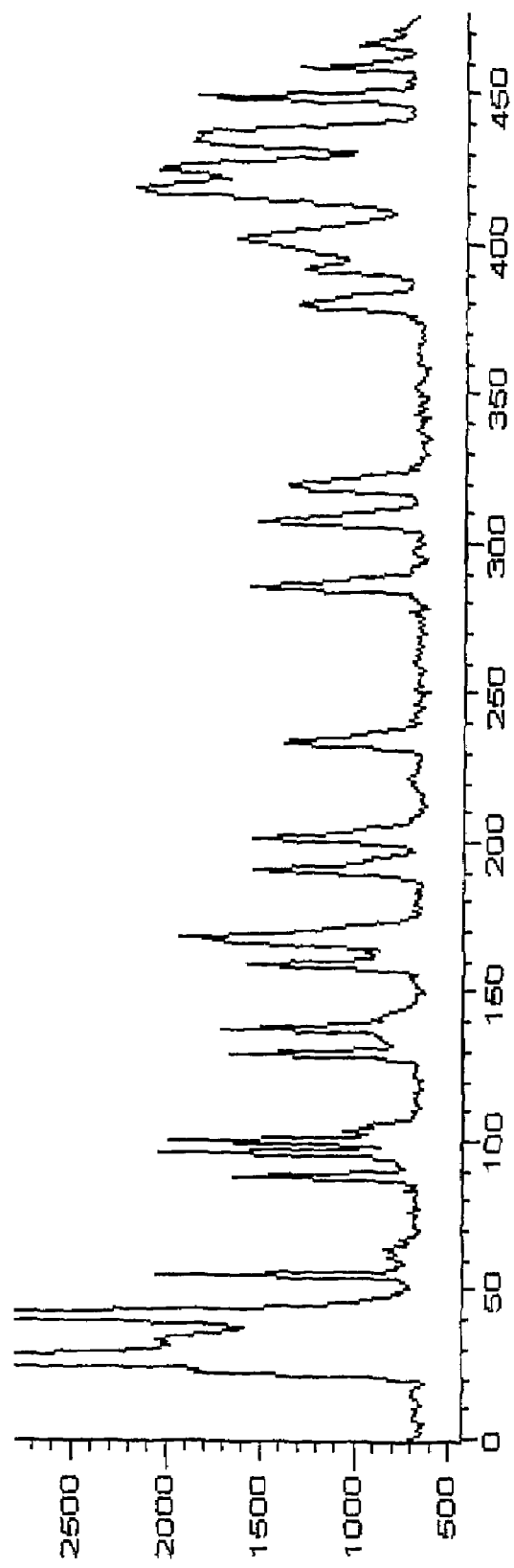
FIG. 5 shows the single color M13 standard separation trace obtained on the vertical T design micro-channel chip, with capillary injection.

FIG. 5 shows the single color M13 standard separation trace obtained by this technique.

Example 2

Sample Separation Using Pen Injection

An electrode board was made to compare the pen loading/injection with conventional chip injection method. For the row of sample electrodes, every other electrode was replaced with a loading pen.

A 6" microfluidic chip with conventional twin-T injector design was prepared for an electrophoresis separation. The sample wells corresponding to the Platinum injection electrodes were filled with a FITC dye solution and the sample wells corresponding to spotter pens were filled with water. Before injection, the pens were dipped into the same FITC dye solution. The electrode board was then placed on top of the chip, lowered until the pens/electrodes were in contact with the sample wells, and the injection and separation were run in a standard mode.

Figure 6:
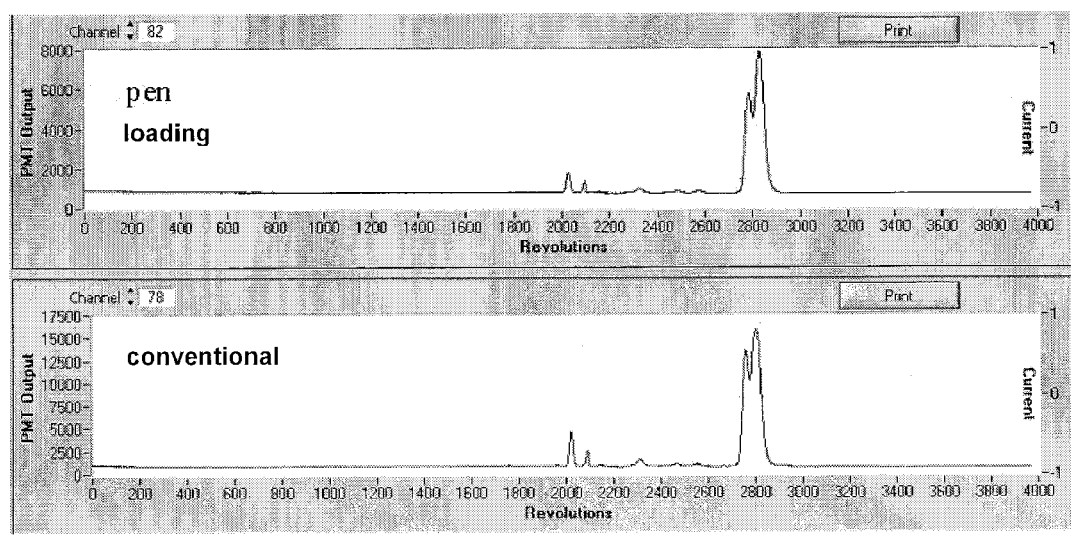
FIG. 6 shows the traces from both a conventional loading and a pen-injection/loading channel.

FIG. 6 shows the traces from a conventional loading and a pen-injection/loading channel. It can be seen that peak distribution is identical. The signal intensity is surprisingly strong for only 50 nl of pen-injected sample, in comparison to 1.5 μl sample in the regular sample well. The experiment proves that these pens can be used for loading and injecting samples on microchips.

Example 3

Sample Separation Using the Vertical T Design and Pen Injection

The overall lay out of the chip is as shown in FIG. 1A. No waste port was drilled for this chip. First, a glass wafer was etched by using the standard 16-channel protocol. Two mm cathode and anode holes were drilled. 0.75 mm holes were drilled at 5 mm, down-stream to cathode.

The chip was derivatized and loaded with LPA matrix by using a high pressure clamping/loading system. A shippable one PMT/blue laser breadboard was adapted for scanning this chip. The detection window was for T-ROX trace only.

The sample injection/separation was performed in the following sequence. First, the chip was rinsed in DI water. Then the chip was aligned on the scanning stage. The anode wells were loaded with buffer and electrodes. Samples were then picked up by an array of pens as described. The pens were then aligned with the loading ports, and lowered to allow physical contact between the pen and the separation matrix. Sample were then injected (0.4 kV; 40 s). The ports were rinsed with DI water. The cathode port is loaded with electrode and buffer. Finally the samples were separated at 1.4 kV for about 15 min.

Figure 7:
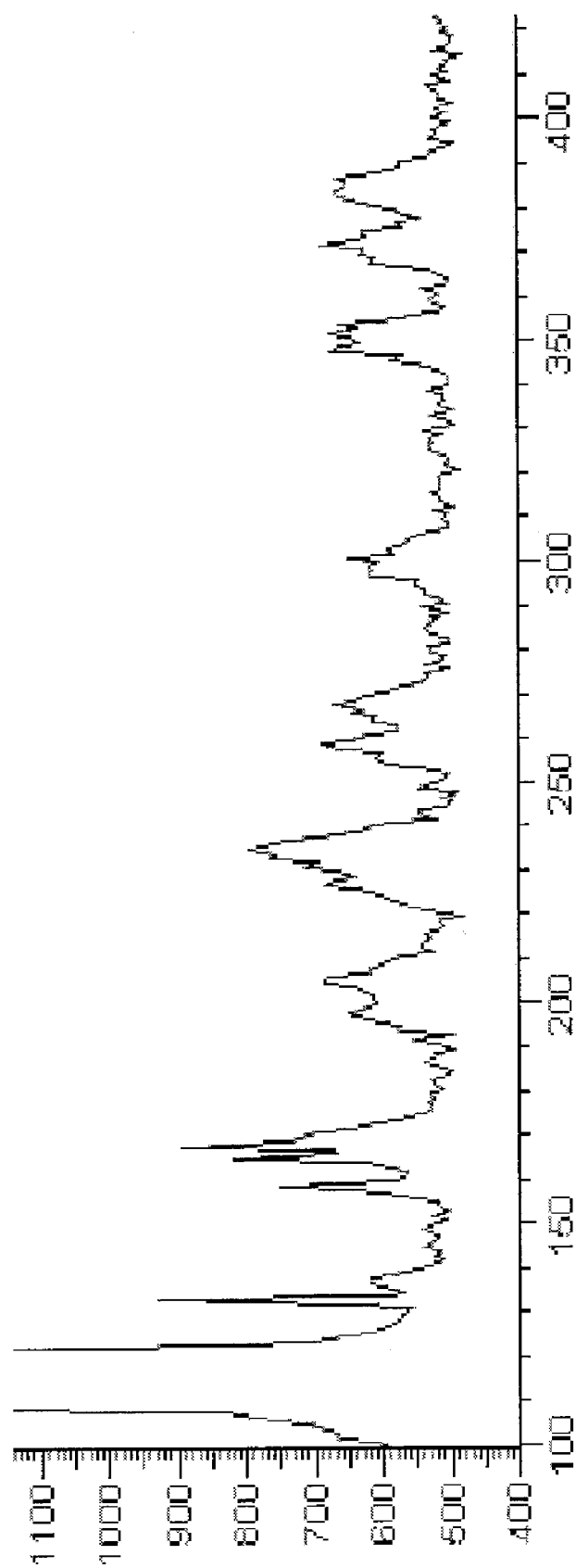
FIG. 7 shows the electropherogram of a ROX labeled ladder, obtained by the above pen injectionlsample separation method.

FIG. 7 shows the electropherogram of a ROX labeled ladder, obtained by the above pen injection/sample separation method. The experiment proved that the spotter pen could be used for loading and injecting samples for the high density microchip of the vertical T design.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A high density capillary array electrophoresis plate comprising:
   an array of parallel microfabricated separation channels formed on a surface of a first microfabricated substrate and a corresponding surface of a second substrate bonded to the surface of said first substrate, each of said channels having a first end and a second end;
   an array of sample ports on a first surface of said capillary array electrophoresis plate;
   an array of sample passageways connecting said array of sample ports and said array of separation channels, wherein each of said array of sample passageways is perpendicular to said first surface of said capillary array electrophoresis plate;
   an array of waste ports on a second surface of said capillary array electrophoresis plate;
   an array of waste passageways connecting said array of waste ports and said array of separation channels, wherein each of said array of waste passageways is perpendicular to said second surface of said capillary array electrophoresis plate;
   a waste reservoir mount mounted on said second surface of said capillary array electrophoresis plate; and
   at least one electrode coupleable to said waste reservoir mount;
   wherein each separation channel of the plurality of separation channels is in fluid communication with at least one dedicated sample port through one of said array of sample passageways, and is in fluid communication with said waste reservoir through one of said array of waste ports.

2. The capillary array electrophoresis plate of claim 1, wherein each of said array of sample passageways and each of said array of waste passageways forms a single passageway, connecting to one of said array of microfabricated separation channels.

3. The capillary array electrophoresis plate of claim 1 wherein said array of sample ports are regularly spaced on the plate and adapted to engage a parallel loading device.

4. The capillary array electrophoresis plate of claim 3, wherein the parallel loading device comprises an array of capillaries.

5. The capillary array electrophoresis plate of claim 3, wherein the parallel loading device comprises an array of metal pens.

6. The capillary array electrophoresis plate of claim 1 further comprising:
   an array of cathode ports on the first surface of said capillary array electrophoresis plate, each connected to said first end of each of the separation channels; and
   an array of anode ports on the first surface of said capillary array electrophoresis plate, each connected to said second end of each of the separation channels.

7. The capillary array electrophoresis plate of claim 6 further comprising:
   electrode arrays coupleable to each of said cathode and anode ports.

8. The capillary array electrophoresis plate of claim 1 further comprising:
   a common cathode reservoir connected to said first end of each of the separation channels;
   a common anode reservoir connected to said second end of each of the separation channels;
   an electrode for said common cathode reservoir; and
   an electrode for said common anode reservoir.

9. The capillary array electrophoresis plate of claim 8 wherein said common anode and cathode reservoirs are enclosed and each has a buffer loading port on the first surface of said capillary array electrophoresis plate.

10. A method of forming a capillary array electrophoresis plate, comprising:
    forming an array of microfabricated separation channels having a first end and a second end;
    forming an array of sample ports on a first surface of said capillary array electrophoresis plate;
    connecting the array of sample ports to the array of microfabricated separation channels through an array of sample passageways;
    forming an array of cathode ports on the first surface of said capillary array electrophoresis plate, each connected to said first end of each of the separation channels;
    forming an array of anode ports on the first surface of said capillary array electrophoresis plate, each connected to said second end of each of the separation channels;
    connecting an electrode array to each of said array of cathode ports;
    connecting an electrode array to each of said array of anode ports;

forming an array of waste ports on a second surface of said capillary array electrophoresis plate;

connecting the array of waste ports and the array of separation channels through an array of waste passageways, wherein each of said array of waste passageways is perpendicular to said second surface of said capillary array electrophoresis plate;

forming a waste reservoir mount;

mounting said waste reservoir mount on said second surface of said capillary array electrophoresis plate; and coupling at least one electrode to said waste reservoir mount;

wherein each separation channel of the plurality of separation channels is in fluid communication with said waste reservoir through one of said array of waste ports.

11. A method of forming a capillary array electrophoresis plate, comprising:

forming an array of microfabricated separation channels having a first end and a second end;

forming an array of sample ports on a first surface of said capillary array electrophoresis plate;

connecting the array of sample ports to the array of microfabricated separation channels through an array of sample passageways;

connecting a common cathode reservoir to said first end of each of said array of separation channels;

connecting a common anode reservoir to said second end of each of said array of separation channels;

connecting an electrode to said cathode reservoir;

connecting an electrode to said anode reservoir;

forming an array of waste ports on a second surface of said capillary array electrophoresis plate;

connecting the array of waste ports and the array of separation channels through an array of waste passageways, wherein each of said array of waste passageways is perpendicular to said second surface of said capillary array electrophoresis plate;

forming a waste reservoir mount;

mounting said waste reservoir mount on said second surface of said capillary array electrophoresis plate; and coupling at least one electrode to said waste reservoir mount;

wherein each separation channel of the plurality of separation channels is in fluid communication with said waste reservoir through one of said array of waste ports.

12. The method of claim 11, wherein a distance from each cathode port to a point where a sample port of said array of sample ports is connected to said channel is approximately equal for each separation channel.

13. The method of claim 10, wherein a distance from each cathode port to a point where a sample port of said array of sample ports is connected to said channel is approximately equal for each separation channel.

* * * * *

UNITED STATES PATENT AND TRADEMARK OFFICE
CERTIFICATE OF CORRECTION

PATENT NO. : 7,651,599 B2  Page 1 of 1
APPLICATION NO. : 10/528864
DATED : January 26, 2010
INVENTOR(S) : Blaga et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1335 days.

Signed and Sealed this

Twenty-eighth Day of December, 2010

David J. Kappos
*Director of the United States Patent and Trademark Office*